Patent Number: 4,590,274
… Date of Patent: May 20, 1986

United States Patent
Cocuzza

[54] ANTIHYPERTENSIVE 1-[BIS-(SUBSTITUTED PHENYL)METHYL]-4[2-(1,2,3,4-TETRAHYDRO-SUBSTITUTED NAPHTHALEN-1-YLIDENE)ETHYL]PIPERAZINES

[75] Inventor: Anthony J. Cocuzza, Wilmington, Del.

[73] Assignee: E. I. Du Pont de Nemours and Company, Wilmington, Del.

[21] Appl. No.: 688,382

[22] Filed: Jan. 3, 1985

[51] Int. Cl.$^4$ ............... C07D 295/02; A61K 31/495
[52] U.S. Cl. ........................... 544/396; 544/378; 549/359
[58] Field of Search ............... 544/378, 396; 514/255

[56] References Cited

U.S. PATENT DOCUMENTS 4,130,646 12/1978 Vogt et al. ................. 544/392
4,148,897 4/1979 Oka et al. .................. 544/396
4,199,582 4/1980 Oka et al. .................. 544/396

FOREIGN PATENT DOCUMENTS 820485 1/1975 Belgium .
0000395 1/1979 European Pat. Off.
36478 4/1975 Japan ................... 544/396

Primary Examiner—Donald G. Daus
Assistant Examiner—Cecilia Shen

[57] ABSTRACT

Antihypertensive piperazineethylidenebenzocycloalkanes are provided. These compounds have the formula:

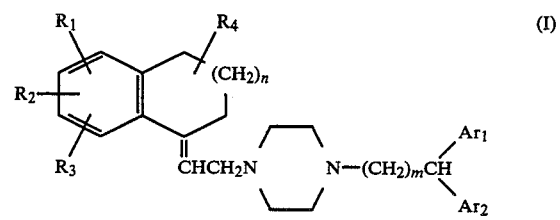

wherein
 $R_1$, $R_2$ and $R_3$ are independently $C_1$–$C_6$ alkyl, hydrogen, $C_1$–$C_6$ alkoxy, hydroxy, or halo, or $R_1$ and $R_2$ or $R_2$ and $R_3$ together can form a methylenedioxy bridge;
 $R_4$ is H or $C_1$–$C_6$ alkyl;
 n is 0, 1 or 2;
 m is 0, 1, 2 or 3; and
 $Ar_1$ and $Ar_2$ are independently phenyl optionally substituted with one or two of halogen, hydroxy, or $C_1$–$C_6$ alkoxy groups,
or a pharmaceutically acceptable salt thereof.

24 Claims, No Drawings

ANTIHYPERTENSIVE 1-[BIS-(SUBSTITUTED PHENYL)METHYL]-4[2-(1,2,3,4-TETRAHYDRO-SUBSTITUTED NAPHTHALEN-1-YLIDENE)ETHYL]PIPERAZINES

BACKGROUND OF THE INVENTION

1. Field of Invention

This invention relates to piperazineethylidenebenzocycloalkanes, pharmaceutical compositions containing them, and methods of using them to treat hypertension.

2. Prior Art

U.S. Pat. No. 4,130,646 issued to Vogt et al. on Dec. 19, 1978 discloses amongst others (1)-phenyl-(4)-substituted piperazines of the formula:

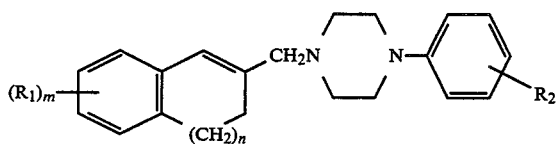

where $R_1$ is hydrogen, halogen, hydroxy, alkanoyloxy, alkoxy, alkylthio, alkyl, $CF_3$ or $-OCH_2O-$; $R_2$ is hydrogen, halogen, alkyl, alkoxy, alkylthio or $CF_3$; m is 1, 2; and n is an integer of 0–2. The compounds are stated to be sedatives, muscle relaxants and neuroleptics.

Belgian Pat. No. 820,485 discloses dibenzo(a,e)cyclopropa(c)cycloheptene derivatives, useful as antidepressants and diuretics, of the formula:

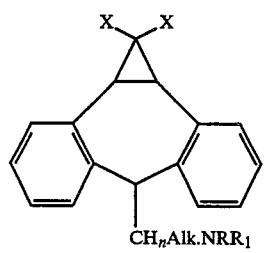

where Alk represents ethylene or propylene; $NRR_1$ can be amonst others 4-methylpiperazino, 4-(2-hydroxyethyl)piperazine; and n is an integer of 1 or 2 depending on whether the dotted line is a single or double bond.

U.S. Pat. No. 4,199,582 issued to Oka et al on Apr. 22, 1980 discloses dihydronaphthalene compounds, useful as antihypertensives, for management of impaired cerebral circulation and as peripheral vasodilators. These compounds have the formula:

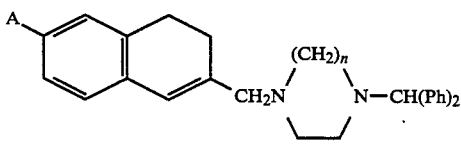

where A is di($C_{1-4}$ alkyl)amino, or a 5–7 membered cyclic amino group, which may contain one oxygen; and n is an integer of 2 or 3.

A number of other references disclose piperazine derivatives which possess antihypertensive activity. One such reference is European Pat. No. 395 which discloses 2-(1-piperazinyl)tetralin compounds of the formula:

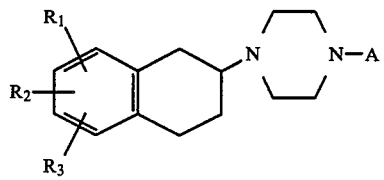

where $R_1$ can be hydroxy, $C_{1-4}$ alkoxy, $C_{1-20}$ alkanoyloxy, $R_2$ and $R_3$ are each hydrogen or as $R_1$, or $R_1$ and $R_2$ on adjacent carbon atoms can be $-OCH_2O-$, and A is naphthyl.

U.S. Pat. No. 4,148,897 issued to Oka et al. discloses 1,2-dihydronaphthalenes, effective as cerebral and peripheral vasodilators, of the formula:

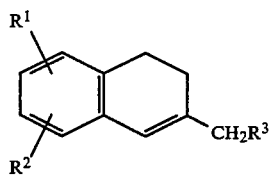

where $R^3$ is piperazinyl or morpholino which amonst others can both optionally be substituted with aralkyl.

Numerous antihypertensive agents of other chemical structures are known in the art. There is nevertheless a continuing need for additional antihypertensive agents because of the various side effects which can occur with existing agents.

SUMMARY OF THE INVENTION

According to the present invention there is provided a compound having the formula:

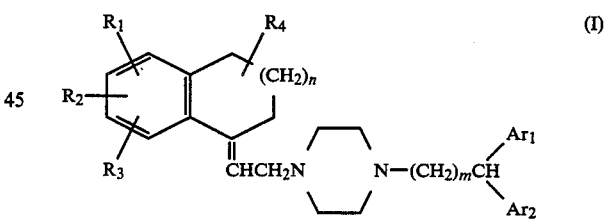

wherein $R_1$, $R_2$ and $R_3$ are independently $C_1$-$C_6$ alkyl, hydrogen, $C_1$-$C_6$ alkoxy, hydroxy, or halo, or $R_1$ and $R_2$ or $R_2$ and $R_3$ together can form a methylenedioxy bridge;

$R_4$ is H or $C_1$-$C_6$ alkyl;

n is 0, 1 or 2;

m is 0, 1, 2 or 3; and $Ar_1$ and $Ar_2$ are independently phenyl optionally substituted with one or two of halogen, hydroxy, or $C_1$-$C_6$ alkoxy groups, or a pharmaceutically acceptable salt thereof.

There is also provided a pharmaceutical composition containing an effective antihypertensive amount of at least one of the above-mentioned compounds, and a method of using the compounds to treat hypertension in a mammal.

PREFERRED EMBODIMENTS

Preferred compounds are those of formula (I) wherein $R_1$, $R_2$ and $R_3$ are independently H, $CH_3$ or $OCH_3$, with at least one and preferably at least two being H; or $R_4$ is H or $CH_3$; or $Ar_1$ and $Ar_2$ are independently phenyl or fluorophenyl.

In addition to antihypertensive activity, selected compounds of this invention have demonstrated activity as calcium entry blockers. This is demonstrated by their ability to effectively inhibit in vitro K+ induced smooth muscle contraction and to inhibit in vitro $^3$H-nitredipine binding acccording to the procedure of Triggle et al. [*Biochemical and Biophysical Research Communications*, 104, 1604 (1982); *Canadian Journal of Physiology and Pharmacology*, 57, 333 (1979).]

The cardiac depressant action of the compounds of this invention can be used potentially to provide useful control of certain cardiac arrhythmics. Therapeutic applications of the compounds of this invention include the treatment of atrial fibrillation and flutter, paroxysmal supraventricular and ventricular tachycardias, and premature systoles.

Synthesis

The compounds of this invention (Formula I) can be prepared via a two-step procedure from 1-hydroxy-1-ethenylbenzocycloalkanes of the general Formula (II), as is depicted in Scheme A:

Scheme A

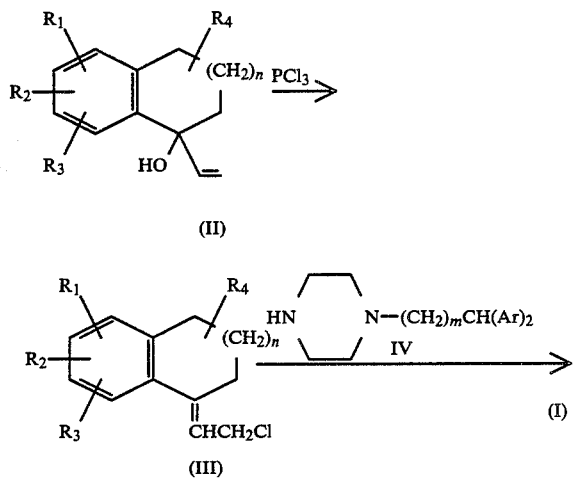

Methods of preparation of 1-hydroxy-1-ethenylbenzocycloalkanes are described in Crippin, D. J. et al., *J. Chem. Soc.* (C), 10, 1970 and Nazarov, I. N. et al., *Dokladi Akad. Nauk. SSR*, 112, 1067 (1957), i.e., treatment of the corresponding benzocycloalkan-1-ones with vinyl magnesium bromide or vinyl lithium.

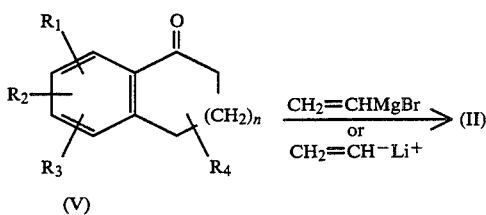

Low temperature treatment of 1-hydroxy-1-ethenyl-benzocycloalkanes of Formula (II) with phosphorus trichloride, in an inert solvent such as methylene chloride, ether, tetrahydrofuran, or the like affords the corresponding alkyl halide of Formula (III). A reaction temperature of from $-60°$ C. to $-40°$ C. is preferred. Phosphorus tribromide may be substituted however more favorable results are obtained with phosphorus trichloride.

The allyl chlorides (Formula III) may be isolated, however it is preferred to treat the compounds immediately following preparation with the requisite diaralkyl piperazines of general Formula (IV) because the allyl chlorides undergo rearrangement to give the isomer where the double bond has migrated to the endocyclic position. This acid-catalyzed rearrangement is successfully avoided by treating the allyl chloride in situ with piperazines of Formula (IV).

The synthesis of diaralkyl piperazines (Formula IV) is described in British Pat. No. 1268710; U.S. Pat. No. 4,250,176; and U.S. Pat. No. 3,267,104. Most conveniently, the piperazines are prepared from 1-ethoxycarbonyl piperazine.

The compounds of Formula (I) can be prepared by reacting the allyl chlorides of Formula (III) with a monosubstituted piperazine of Formula (IV) in a polar solvent such as 4-methyl-2-pentanone at a temperature between 25° C. and the reflux temperature of the solvent in the presence of an inorganic base such as potassium carbonate. The use of a catalytic amount of potassium iodide is preferred.

Both the E and Z isomers are included in the scope of this invention. Where the products of this invention exist as mixtures of diastereomers, the E and Z isomers can be separated by methods well known in the art; e.g., chromatography.

Salts of compounds of Formula (I) are formed by procedures well known to those skilled in the art. The dihydrochloride salts are preferred, but other salts can be prepared from acids such as sulfuric, acetic, tartaric, maleic acid and the like.

The invention can be further understood by the following examples in which parts and percentages are by weight and temperatures are in degrees Centigrade.

EXAMPLE 1

1-[Bis(4-fluorophenyl)methyl]-4-[2-(1,2,3,4-tetrahydro-5-methoxynaphthalene-1-ylidene)ethyl]piperazine dihydrochloride Part (A)

1-Hydroxy-1-ethenyl-5-methoxy-1,2,3,4-tetrahydronaphthalene

To a stirred mixture of 1.5 g of magnesium turnings and a crystal of iodine in 15 ml of dry tetrahydrofuran under nitrogen was added 5.6 ml of vinylbromide in 10 ml of dry tetrahydrofuran dropwise. The reaction temperature was maintained between 40°–50° using an ice-water bath. This mixture was refluxed for 30 minutes and then cooled to room temperature. A solution of 8 g of 5-methoxy-1-tetralone in 30 ml of dry tetrahydrofuran was added dropwise over a 15 minute period. The reaction was stirred for 1 hour at room temperature and then poured onto aqueous ammonium chloride. This mixture was extracted twice with methylene chloride and the combined extracts were washed with brine, dried over sodium sulfate and evaporated to give 9.2 g of crude product. The title compound was purified by evaporative distillation at 85° to give 7.63 g of product as a colorless syrup.

NMR (200 MHz, CDCl$_3$): δ 1.75–2.0 (m, 4H), 2.5–3.0 (m, 2H), 3.78 (s, 3H), 5.1–5.3 (m, 2H), 6.0 (dd, 1H, J=17, 10 Hz), 6.72 (d, 1H, J=8 Hz) and 6.9–7.2 (m, 2H).

The following compounds were prepared analogously:
(a) 1-hydroxy-1-ethenyl-1,2,3,4-tetranaphthalene (8.03 g), starting from 10 g of α-tetralone;
(b) 1-hydroxy-1-ethenylindane (6.44 g), starting from 9 g of indanone; and
(c) 1-hydroxy-1-ethenylbenzocycloheptane (7.8 g), starting from 10.8 g of benzosubesone.

Part (B)

1-[Bis(4-fluorophenyl)methyl]-4-[2-(1,2,3,4-tetrahydro-5-methoxynaphthalen-1-ylidene)ethyl]piperazine dihydrochloride A 250 ml flask fitted with a nitrogen inlet and a dropping funnel was charged with 3.5 ml of distilled phosphorus trichloride, 50 ml of methylene chloride and 20 drops of pyridine. The reaction mixture was cooled to −40°, and a solution of 10 g of 1-hydroxy-1-ethenyl-5-methoxy-1,2,3,4-tetrahydronaphthalene in 30 ml of methylene chloride was added dropwise over 20 minutes. After the addition was complete, the mixture was stirred for 1 hour at −40°, and then poured onto 250 ml of ice cold ether. The ether layer was washed with brine and dried over sodium sulfate. N-[Bis(4-fluorophenyl)methyl]piperazine (8.5 g) was added and the mixture was evaporated to dryness. Pulverized potassium carbonate (20 g) and 200 ml of 4-methyl-2-pentanone were added to the reaction flask, and the mixture was stirred at room temperature for 3 hours. The reaction mixture was filtered and concentrated to dryness. The crude product was purified by flash chromatography on silica gel by elution with 3% methanol in methylene chloride to give 6.53 g of the free base of the title compound as a pale yellow oil.

NMR (200 MHz, CDCl$_3$): δ 1.60–1.90 (m, 3H), 2.3–2.6 (m, 9H), 2.70 (t, 2H, J=6 Hz), 3.2 (d, 2H, J=6 Hz), 3.80 (s, 3H), 4.21 (s, 1H), 6.04 (t, 1H, J=6 Hz) and 6.6–7.4 (m, 12H).

Treating the free base in a mixture of methylene chloride with methanolic hydrogen chloride and then adding ether gave 6.0 g of the dihydrochloride salt. This was further purified by recrystallization from ethanol, (m.p. 184°–186°).

EXAMPLE 2

1-[Bis(4-fluorophenyl)methyl]-4-[2-(2,3-dihydro-1H-inden-1-ylidene)ethyl]piperazine To a solution of 175 μl of distilled phosphorus trichloride and 200 μl of pyridine in 5 ml of methylene chloride at −60° under nitrogen was added dropwise a solution of 800 mg of 1-hydroxy-1-ethenylindane in 3 ml of methylene chloride over a 10 minute period. After addition was complete, the mixture was stirred at −60° for 1 hour and was then poured onto 50 ml of ice-cold aqueous sodium bicarbonate. This mixture was extracted with 50 ml of ice-cold ether and the extracts were dried over sodium sulate. N-[Bis(4-fluorophenyl)methyl]piperazine (700 mg) and 2 g of pulverized potassium carbonate was added, and the mixture was evaporated to dryness. Potassium iodide (20 mg) and 20 ml of 4-methylpentanone were added, and the mixture was refluxed overnight under nitrogen. The cooled mixture was filtered and the filtrate was washed with brine, dried over sodium sulfate and evaporated to dryness. The crude product was purified by flash chromatography on silica gel by elution with 5% methanol in methylene chloride to give 241 mg of the title compound as a colorless solid, m.p. 138°–142°.

NMR (200 MHz, CDCl$_3$): δ 2.3–2.7 (m, 8H), 2.78 (m, 2H), 3.0 (m, 2H), 3.18 (d, 2H, J=7 Hz), 4.25 (s, 1H), 6.02 (t, 1H, J=7 Hz) and 6.9–7.5 (m, 12H).

EXAMPLE 3

1-[(4,4-Diphenyl)butyl]-4-[2-(1,2,3,4-tetrahydronaphthalene-1-ylidene)ethyl]piperazine dihydrochloride Part (A)

N-(4,4-Diphenylbutyl)piperazine

A mixture of 20 g of 4,4-diphenyl-1-chlorobutane, 15 g of ethyl piperazinecarboxylate, 8 g of potassium carbonate, 400 mg of potassium iodide and 140 ml of 4-methyl-2-pentanone was refluxed under nitrogen overnight. The cooled mixture was filtered, and the filtrate was washed with water, dried, and evaporated. Volatile impurities were removed by evaporative distillation at 0.1 mm, 170°.

A mixture of 26 g of this crude product, 300 ml of 95% ethanol, and 70 g of potassium hydroxide was refluxed for 1.75 hours. The cooled mixture was evaporated to a small volume and partitioned between water and ether. The aqueous fraction was extracted with ether and the combined ether layers were washed with brine, dried, and evaporated. Volatile impurities were removed by evaporative distillation at 0.1 mm/90°. Crystallization of the residue from cold petroleum ether afforded 11.47 g of N-(4,4-diphenylbutyl)piperazine as colorless crystals.

Part (B)

1-[(4,4-Diphenyl)butyl]-4-(1,2,3,4-tetrahydronaphthalene-1-ylidene)ethyl]piperazine dihydrochloride To a solution of 350 μl of distilled phosphorus trichloride and 4 drops of pyridine in 10 ml of methylene chloride at −60° under nitrogen was added dropwise a solution of 1.7 g of 1-hydroxy-1-ethenyl-1,2,3,4-tetrahydronaphthalene in 6 ml of methylene chloride over a 15 minute period. This mixture was stirred for 1 hour at −60° and then poured onto ice-cold aqueous sodium bicarbonate. The mixture was extracted with ice-cold ether and the extract was washed with brine and dried over sodium sulfate and magnesium sulfate. N-(4,4-diphenylbutyl)piperazine (1.7 g) and 4 g of pulverized potassium carbonate were added, and the mixture was evaporated to dryness. Potassium iodide (40 mg) and 40 ml of 4-methyl-2-pentanone were added to the reaction flask and the mixture was refluxed for 4 hours under nitrogen. The cooled mixture was filtered and the filtrate was washed with water, and brine, dried over sodium sulfate and evaporated to dryness. The crude product was purified by flash chromatography on silica gel by elution with 5% methanol in methylene chloride to give 1.6 g of the product as a yellow oil.

NMR (360 MHz, CDCl$_3$): δ 1.47 (m, 2H), 1.81 (m, b 2H), 2.05 (m, 2H), 2.36 (t, 2H, J=7 Hz), 2.3–2.4 (m, 8H), 2.50 (t, 2H, J=7 Hz), 2.77 (t, 2H, J=6 Hz), 3.18 (d, 2H, J=7 Hz), 3.89 (t, 1H, J=7 Hz), 6.08 (t, 1H, J=7 Hz), 7.05–7.3 (m, 13H) and 7.59 (m, 1H).

EXAMPLES 4 AND 5

1-[Bis(4-fluorophenyl)methyl]-4-[2-(6,7,8,9-tetrahydro-5H-benzocyclohepten-5-ylidene)ethyl]piperazine; E and Z isomers To a solution of 155 μl of freshly distilled phosphorus trichloride and 2 drops of pyridine in 5 ml of methylene chloride at −60° under nitrogen was added dropwise a solution of 850 mg of 1-hydroxy-1-ethenylbenzocycloheptane in 3 ml of dry methylene chloride over a 10 minute period. After addition was complete, the mixture was stirred for 1 hour at −60° and then poured onto ice-cold aqueous sodium bicarbonate. This mixture was extracted with ether and the extracts were dried and evaporated. N-[Bis(4-fluorophenyl)methyl]-piperazine (700 mg), 2 g of potassium carbonate, 25 mg of potassium iodide, and 25 ml of 4-methyl-2-pentanone were added to the reaction and the mixture was refluxed for 1 hour. The cooled mixture was filtered and the filtrate was washed sequentially with water and brine, and then dried over sodium sulfate and evaporated. The crude product contained 2 major components which were purified and separated by flash chromatography on silica gel by elution with ether-petroleum ether (4:1). The first compound to elute from the column was assigned the structure of the E isomer of the title compound (350 mg).

NMR (200 MHz, CDCl$_3$) δ 1.75 (broad s, 4H), 2.3–2.8 (m, 12H), 3.15 (d, 2H, J=7 Hz), 4.26 (s, 1H), 5.5 (t, 1H, J=7 Hz) and 6.9–7.5 (m, 12H).

The dihydrochloride salt, m.p. 240°–245°, was prepared with dry hydrogen chloride in methanol.

The second compound to elute from the column was assigned the structure of the Z-isomer of the title compound (461 mg) as a colorless glass.

NMR (200 MHz, CDCl$_3$): δ 1.7 (m, 2H), 1.8 (m, 2H), 2.2–2.6 (m, 8H), 2.68 (m, 2H), 2.9 (d, 2H, J=7 Hz), 4.20 (s, 1H), 5.60 (t, 1H, J=7 Hz) and 6.9–7.5 (m, 12H).

EXAMPLE 6

1-[Bis(4-fluorophenyl)methyl]-4-[2-(1,2,3,4-tetrahydronaphthalen-1-ylidene)ethyl]piperazine dihydrochloride

Part (A)

1-(2-Chloroethylideno)-1,2,3,4-tetrahydronaphthalene

To a solution of 175 μl of freshly distilled phosphorus trichloride and 2 drops of pyridine in 5 ml of methylene chloride at −60° under nitrogen was added dropwise a solution of 850 mg of 1-ethenyl-1-hydroxy-1,2,3,4-tetrahydronaphthalene over a 10 minute period. After the addition was complete, the mixture was stirred for 1 hour at −60°, and then poured onto aqueous sodium bicarbonate. This mixture was extracted with ether and the organic layer was dried and evaporated to give 779 mg of 1-(2-chloroethylideno)-1,2,3,4-tetrahydronaphthalene as an oil contaminated (~12%) with the isomer in which the double bond has moved into the ring.

NMR (200 MHz, CDCl$_3$): δ 1.9 (m, 2H), 2.6 (m, 2H), 2.8 (m, 2H), 4.3 (d, 2H, J=7 Hz), 6.2 (t, 1H, J=7 Hz) and 7.0–7.7 (m, 4H).

Part (B)

1-[Bis(4-fluorophenyl)methyl]-4-[2-(1,2,3,4-tetrahydronaphthalene-1-ylidene)ethyl]piperazine dihydrochloride A mixture of 799 mg of 1-(2-chloroethylideno)-1,2,3,4-tetrahydronaphthalene, 850 mg of N-[bis(4-fluorophenyl)methyl]piperazine, 2 g of potassium carbonate, 20 mg of potassium iodide and 25 ml of 4-methyl-2-pentanone was refluxed under N$_2$ for 4.75 hours. The cooled mixture was filtered, and the filtrate was washed with water and evaporated. The crude product was purified by flash chromatography on silica gel by elution with ether-methylene chloridemethanol (50:48:2) to give 674 mg of a glass. The dihydrochloride salt was prepared by adding ethereal hydrogen chloride to a methylene chloride solution of the free base, evaporating the solvent, and triturating the residue with ethyl acetate to give 680 mg of the title compound as colorless crystals, m.p. 219°–221°.

NMR (200 MHz, CDCl$_3$): δ 1.82 (m, 2H), 2.55 (t, 2H, J=6 Hz), 2.80 (t, 2H, J=6 Hz), 3.55 (m, 4H), 3.98 (m, 4H), 4.30 (m, 2H), 5.35 (s, 1H), 6.22 (t, 1H, J=7 Hz) and 7.0–8.1 (m, 12H).

EXAMPLE 7

1[Bis(4-fluorophenyl)methyl]-4-(1,2,3,4-tetrahydro-5,7-dimethylnaphthalen-1-ylidene)ethyl]piperazine dihydrochloride

Part (A)

1-Hydroxy-1-ethenyl-5,7-dimethyl-1,2,3,4-tetrahydronaphthalene

To a stirred mixture of 3.5 g of magnesium turnings and a few crystals of iodine in 150 ml of dry tetrahydrofuran under nitrogen was added dropwise 13 ml of vinyl bromide. The reaction temperature was maintained between 40°–50° using an ice-water bath. This mixture was stirred at room temperature for one hour before a solution of 6.3 g of 5.7-dimethyl-1-tetralone in 50 ml of dry tetrahydrofuran was added dropwise. This reaction mixture was stirred at room temperature for three hours and then poured onto ice-cold aqueous ammonium chloride. This mixture was extracted with ethyl ether (3×300 ml) and the combined organic solvents were washed with brine (1×100 ml), dried over magnesium sulfate and concentrated to give 5.8 g of a light brown oil. This crude product was purified by reduced pressure distillation (110°/0.3 mm) to give 4.9 g of 1-hydroxy-1-ethenyl-5,7-dimethyl-1,2,3,4-tetrahydronaphthalene as a colorless oil.

NMR (200 MHz, CDCl$_3$): δ 1.90 (m, 4H), 2.10 (s, 3H), 2.15 (s, 3H), 2.60 (m, 2H), 5.09 (dd, 1H, J=10,2 Hz), 5.15 (dd, 1H, J=18,2 Hz), 6.02 (dd, 1H, J=18,10 Hz), 6.90 (s, 1H) and 7.01 (s, 1H).

Part (B)

1-[Bis(4-fluorophenyl)methyl]-4-[2-(1,2,3,4-tetrahydro-5,7-dimethylnaphthalene-1-ylidene)ethyl]-piperazine dihydrochloride To a solution of 1 ml of freshly distilled phosphorus trichloride in 20 ml of distilled methylene chloride at −78° under nitrogen was added dropwise a solution of 4.9 g of 1-hydroxy-1-ethenyl-5,7-dimethyl-1,2,3,4-tetranaphthalene and 0.3 ml of dry pyridine in 15 ml of distilled methylene chloride. This reaction mixture was stirred for 1 hour at −78° and then poured onto 200 ml of ice-cold saturated aqueous sodium bicarbonate. This mixture was extracted with methylene chloride. The combined organic phases were washed with cold brine, dried over sodium sulfate, and filtered. To this filtrate was added 6.2 g of N-[bis(4-fluorophenyl)methyl]piperazine and 6.0 g of potassium carbonate. This mixture was evaporated to dryness under reduced pressure. The solid residue was dissolved in 60 ml of 4-methylpentanone containing 300 mg of potassium iodide and the mixture was refluxed under nitrogen for 6 hours. After cooling to room temperature, the reaction mixture was filtered. The filtrate was washed with brine, dried over magnesium sulfate and concentrated to dryness. The crude product was purified by flash column chromatography on silica gel by elution with 70% diethyl ether in petroleum ether to give 2.2 g of the free base of the title compound as a colorless glass. The dihydrochloride salt was prepared by adding ethereal hydrogen chloride to a methylene chloride solution of the free base, evaporating the solvent, and triturating the residue with ethyl acetate to give 2.15 g of the title compound as a white crystalline solid, m.p. 180°–184°.

NMR (200 MHz, CDCl$_3$): δ 1.80 (m, 2H), 2.09 (s, 3H), 2.15 (s, 3H), 2.51 (m, 12H), 3.10 (d, 2H, J=7.3 Hz), 4.14 (s, 1H), 6.02 (t, 1H, J=7.3 Hz) and 7.10 (m, 10H).

EXAMPLE 8

1-[Bis(4-fluorophenyl)methyl]-4-[2-(1,2,3,4-tetrahydro-7-methoxynaphthalen-1-ylidene)ethyl]piperazine dihydrochloride Following the procedure of Example 7, starting with 6 g of 7-methoxy-1-tetralone, yielded 4.7 g of the title compound as a white glass. The dihydrochloride salt (m.p. 186°–190°) was prepared with ethereal hydrogen chloride.

NMR (60 MHz, CDCl$_3$): δ 1.90 (m, 2H), 2.60 (m, 12H), 3.17 (d, 2H, J=7.2 Hz), 3.90 (s, 3H), 4.20 (s, 1H), 6.10 (t, 1H, J=7.2 Hz) and 7.10 (m, 11H).

EXAMPLE 9

1-[Bis(4-fluorophenyl)methyl]-4-[2-(1,2,3,4-tetrahydro-4-methylnaphthalen-1-ylidene)ethyl]piperazine dihydrochloride Following the procedure of Example 7, starting with 5.5 g of 3-methyl-1-tetralone, yielded 1.5 g of the free base of the title compound. The dihydrochloride salt (m.p. 204°–206°) was prepared with ethereal hydrogen chloride.

NMR (200 MHz, CDCl$_3$): δ 1.87 (m, 2H), 1.15 (d, 3H, J=7.3 Hz), 2.5 (m, 13H), 4.16 (s, 1H), 5.87 (t, 1H, J=4.6 Hz), 6.99 (m, 4H) and 7.19 (m, 8H).

EXAMPLE 10

1-[Bis(4-fluorophenyl)methyl]-4-[2-(1,2,3,4-tetrahydro-2-methylnaphthalen-1-ylidene)ethyl]piperazine dihydrochloride Following the procedure of Example 7, starting with 4.5 g of 2-methyl-1-tetralone, yielded 2.1 g of the title compound.

NMR (200 MHz, CDCl$_3$): δ 1.02 (d, 3H, J=8.1 Hz), 1.70 (m, 2H), 2.50 (m, 10H), 3.18 (m, 3H), 4.22 (s, 1H), 5.98 (t, 1H, J=7.3 Hz) and 7.12 (m, 12H).

The following compounds were prepared or can be prepared by the procedure given in Examples 1–10.

TABLE I

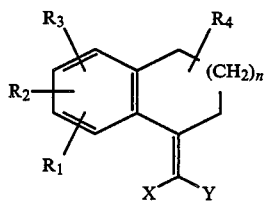

| Ex. No. | $R_1$ | $R_2$ | $R_3$ | $R_4$ | n | X | Y | m.p. °C. |
|---|---|---|---|---|---|---|---|---|
| 1 | 5-OCH$_3$ | H | H | H | 1 | H | CH$_2$N⌒NCH(4-FC$_6$H$_4$)$_2$·2HCl | 184–186 |
| 2 | H | H | H | H | 0 | H | CH$_2$N⌒NCH(4-FC$_6$H$_4$)$_2$ | 138–142 |
| 3 | H | H | H | H | 1 | H | CH$_2$N⌒N⌒CH(C$_6$H$_5$)$_2$·2HCl | 220–225 |
| 4 | H | H | H | H | 2 | H | CH$_2$N⌒NCH(4-FC$_6$H$_4$)$_2$·2HCl | 240–245 |
| 5 | H | H | H | H | 2 | a* | H | glass |

TABLE I-continued

[Structure: substituted bicyclic compound with R₁, R₂, R₃, R₄ substituents on aromatic ring, (CH₂)ₙ group, and =C(X)(Y) exocyclic double bond]

| Ex. No. | R₁ | R₂ | R₃ | R₄ | n | X | Y | m.p. °C. |
|---|---|---|---|---|---|---|---|---|
| 6 | H | H | H | H | 1 | H | CH₂N⌒NCH(4-FC₆H₄)₂·2HCl | 219–221 |
| 7 | 5-CH₃ | 7-CH₃ | H | H | 1 | H | CH₂N⌒NCH(4-FC₆H₄)₂·2HCl | 180–184 |
| 8 | H | 7-OCH₃ | H | H | 1 | H | CH₂N⌒NCH(4-FC₆H₄)₂·2HCl | 186–190 |
| 9 | H | H | H | 4-CH₃ | 1 | b* | H | 204–206 |
| 10 | H | H | H | 2-CH₃ | 1 | H | CH₂N⌒NCH(4-FC₆H₄)₂·2HCl | |
| 11 | H | H | H | 3-CH₃ | 1 | H | CH₂N⌒NCH(4-FC₆H₄)₂·2HCl | |
| 12 | 5-OCH₃ | H | H | H | 0 | H | CH₂N⌒NCH(4-FC₆H₄)₂·2HCl | |
| 13 | 5-OCH₃ | 7-OCH₃ | H | H | 1 | H | CH₂N⌒NCH(4-FC₆H₄)₂·2HCl | |
| 14 | 5-OCH₂CH₃ | H | H | H | 1 | H | CH₂N⌒NCH(4-FC₆H₄)₂·2HCl | |
| 15 | 5-OCH₃ | 7-OCH₃ | H | 2-CH₃ | 1 | H | CH₂N⌒NCH(4-FC₆H₄)₂·2HCl | |
| 16 | 5-OCH₃ | 6-CH₃ | 7-CH₃ | H | 1 | H | CH₂N⌒NCH(4-FC₆H₄)₂·2HCl | |
| 17 | 6-OC₂H₅ | 7-Cl | H | H | 1 | H | CH₂N⌒NCH(4-FC₆H₄)₂·2HCl | |
| 18 | 5-CH₃CH₂ | H | H | H | 1 | c* | H | |

TABLE I-continued

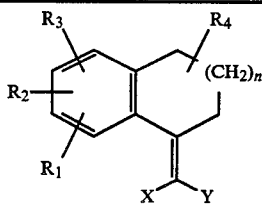

| Ex. No. | $R_1$ | $R_2$ | $R_3$ | $R_4$ | n | X | Y | m.p. °C. |
|---|---|---|---|---|---|---|---|---|
| 19 | 5-OCH$_3$ | 6-CH$_3$ | H | H | 0 | H | CH$_2$N⌒NCH(4-FC$_6$H$_4$)$_2$.2HCl | |
| 20 | 5-OCH$_3$ | H | H | 2-CH$_3$ | 0 | H | CH$_2$N⌒NCH(4-FC$_6$H$_4$)$_2$.2HCl | |
| 21 | 5-CH$_3$CH$_2$CH$_2$ | H | H | H | 1 | H | CH$_2$N⌒NCH(4-FC$_6$H$_4$)$_2$.2HCl | |
| 22 | H | H | H | H | 2 | H | CH$_2$N⌒NCH(4-MeOC$_6$H$_4$)$_2$.2HCl | |
| 23 | 5-OCH$_3$ | H | H | H | 1 | H | CH$_2$N⌒NCH(3,4-FC$_6$H$_4$)$_2$.2HCl | |
| 24 | 5-OCH$_3$ | H | H | 2-CH$_3$CH$_2$ | 1 | H | CH$_2$N⌒NCH(4-FC$_6$H$_4$)$_2$.2HCl | |

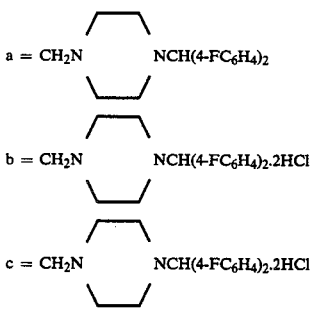

a = CH$_2$N⌒NCH(4-FC$_6$H$_4$)$_2$ b = CH$_2$N⌒NCH(4-FC$_6$H$_4$)$_2$.2HCl c = CH$_2$N⌒NCH(4-FC$_6$H$_4$)$_2$.2HCl

Dosage Forms

The compounds of this invention can be administered in the treatment of hypertension according to the invention by any means that effects contact of the active ingredient compound with the site of action in the body of a warm-blooded animal. For example, administration can be parenteral, i.e., intravenous. Alternately or concurrently, in some cases administration can be by the oral route.

For the purpose of this disclosure, a warm-blooded animal is a member of the animal kingdom possessed of a homeostatic mechanism and includes mammals and birds.

The dosage adminstered will be dependent on the age, health and weight of the recipient, the extent of disease, kind of concurrent treatment, if any, frequency of treatment and the nature of the effect desired. Usually, a daily dosage of active ingredient compound will be from about 0.1 to 100 milligrams per kilogram of body weight. Ordinarily, from 0.2 to 60, and preferably 1.0 to 40, milligrams per kilogram per day in one or more applications per day is effective to obtain desired results. For the more potent compounds of the invention, e.g., the compound of Example 1, the daily dosage ranges are from about 0.1 to 20 mg/kg, preferably 0.2 to 20 mg/kg, and more preferably from 0.5 to 5 mg/kg.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules can contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used as citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc, and 6 milligrams magnesium stearate.

Soft Gelatin Capsules

A mixture of active ingredient in soybean oil is prepared and injected by means of a positive displacement pump into gelatin to form soft gelatin capsules containing 50 milligrams of the active ingredient. The capsules are washed and dried.

Tablets

A large number of tablets are prepared by conventional procedures so that the dosage unit is 50 milligrams of active ingredient, 6 milligrams of magnesium stearate, 70 milligrams of microcrystalline cellulose, 11 milligrams of cornstarch and 27.5 milligrams of lactose. Appropriate coatings may be applied to increase palatability or delay absorption.

Injectable

A parenteral composition suitable for administration by injection is prepared by stirring 1.5% by weight of active ingredient in 10%–60% by volume of co-solvents, like propylene glycol in water. The resultant solution can be sterilized by filtration.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

UTILITY

Spontaneously Hypertensive Rats

The antihypertensive activity of the compounds of this invention is evidenced by tests conducted in spontaneously hypertensive rats (SHR). In one procedure, anesthetized rats are dosed intravenously with graded dose levels of compounds on a cumulative dose schedule. Compounds are administered in an aqueous 0.25% methylcellulose vehicle at a volume to body weight ratio of 1 ml/kg. Arterial blood pressure is continuously recorded directly through an arterial cannula and a polygraph. That dose of compound producing a 30 mm mercury (mm Hg) reduction in mean blood pressure is then determined (effective dose 30). For example, and $ED_{30}$ of 0.16 mg/kg is found for compound of Example 1, 1-[bis(4-fluorophenyl)methyl]-4-[2-(1,2,3,4-tetrahydro-5-methoxynaphthalen-1-ylidene)ethyl]piperazine dihydrochloride.

In a second procedure, graded levels of each compound are administered orally to groups of eight hypertensive rats. The compound is prepared in an aqueous methylcellulose vehicle and administered at a volume to body weight ratio of 5.0 ml/kg. A group of hypertensive rats receiving the aqueous vehicle by the same route serve as controls for each test. At various intervals of time after treatment, usually 90 minutes, the systolic arterial blood pressure of each rat is determined by modification of the microphone-manometer technique (Friedman, M. and Freed, S. C., *Proc. Soc. Exp. Biol. and Med.*, 70, 670 (1949)). That dose of compound which produces a 30 mm mercury reduction in blood pressure when compared to the mean systolic arterial blood pressure of the control animals is then determined. For example, an $ED_{30}$ of 6.5 mg/kg orally is obtained with the compound of Example 1.

Biological results are shown in Table II for the compounds of Examples 1–10.

TABLE II

Antihypertensive Effects in Spontaneously Hypertensive Rats

| Example No. | $ED_{30}$ mg/kg cum. i.v. | $ED_{30}$ mg/kg p.o. |
|---|---|---|
| 1 | 0.16 | 6.5 |
| 2 | 1.4 | >50 |
| 3 | 0.49 | >50 |
| 4 | 0.95 | N.T. |
| 5 | 4.0 | >50 |
| 6 | 1.9 | >50 |
| 7 | 0.73 | <50 |
| 8 | 0.44 | ~46 |
| 9 | 3.7 | >50 |

TABLE II-continued

Antihypertensive Effects in Spontaneously Hypertensive Rats

| Example No. | ED$_{30}$ mg/kg cum. i.v. | ED$_{30}$ mg/kg p.o. |
|---|---|---|
| 10 | 0.15 | >50 |

N.T. = not tested.

As can be seen from Table II, all of the compounds are effective in lowering blood pressure when dosed intraveneously.

What is claimed is:

1. A compound having the formula:

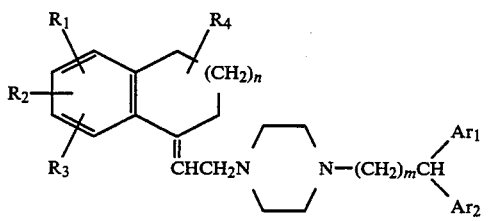 (I)

wherein $R_1$, $R_2$ and $R_3$ are independently n-$C_1$-$C_6$ alkyl, hydrogen, $C_1$-$C_6$ alkoxy, F,Cl,Br, or $R_1$ and $R_2$ or $R_2$ and $R_3$ together can form a methylenedioxy bridge;

$R_4$ is H or $C_1$-$C_6$ alkyl;

n is 0, 1 or 2;

m is 0, 1, 2 or 3; and $Ar_1$ and $Ar_2$ are independently phenyl optionally substituted with one or two of halogen, or $C_1$-$C_6$ alkoxy groups, or a pharmaceutically acceptable salt thereof.

2. A compound of claim 1 wherein $R_1$, $R_2$ and $R_3$ are independently H, $CH_3$ or $OCH_3$ with at least one being H.

3. A compound of claim 1 wherein at least two of $R_1$, $R_2$ and $R_3$ are H.

4. A compound of claim 1 wherein $R_4$ is H or $CH_3$.

5. A compound of claim 1 wherein $Ar_1$ and $Ar_2$ are independently phenyl or fluorophenyl.

6. A compound of claim 1 wherein $R_1$, $R_2$ and $R_3$ are independently H, $CH_3$ or $OCH_3$ with at least one being H; $R_4$ is H or $CH_3$; and $Ar_1$ and $Ar_2$ are independently phenyl or fluorophenyl.

7. A compound of claim 6 wherein $R_4$ is H.

8. The compound of claim 1 which is 1-[bis-(4-fluorophenyl)methyl]-4-[2-(1,2,3,4-tetrahydro-5-methoxynaphthalen-1-ylidene)ethyl]piperazine dihydrochloride.

9. A pharmaceutical composition for treating hypertension consisting essentially of a pharmaceutically acceptable carrier and an effective antihypertensive amount of a compound of claim 1.

10. A pharmaceutical composition consisting essentially of a pharmaceutically acceptable carrier and an antihypertensive amount of a compound of claim 2.

11. A pharmaceutical composition consisting essentially of a pharmaceutically acceptable carrier and an antihypertensive amount of a compound of claim 3.

12. A pharmaceutical composition consisting essentially of a pharmaceutically acceptable carrier and an antihypertensive amount of a compound of claim 4.

13. A pharmaceutical composition consisting essentially of a pharmaceutically acceptable carrier and an antihypertensive amount of a compound of claim 5.

14. A pharmaceutical composition consisting essentially of a pharmaceutically acceptable carrier and an antihypertensive amount of a compound of claim 6.

15. A pharmaceutical composition consisting essentially of a pharmaceutically acceptable carrier and an antihypertensive amount of a compound of claim 7.

16. A pharmaceutical composition consisting essentially of a pharmaceutically acceptable carrier and an antihypertensive amount of the compound of claim 8.

17. A method of treating hypertension in a mammal comprising essentially of administering to a hypertensive mammal an antihypertensive amount of a compound of claim 1.

18. A method of treating hypertension in a mammal consisting essentially of administering to a hypertensive mammal an antihypertensive amount of a compound of claim 2.

19. A method of treating hypertension in a mammal consisting essentially of administering to a hypertensive mammal an antihypertensive amount of a compound of claim 3.

20. A method of treating hypertension in a mammal comprising essentially of administering to a hypertensive mammal an antihypertensive amount of a compound of claim 4.

21. A method of treating hypertension in a mammal consisting essentially of administering to a hypertensive mammal an antihypertensive amount of a compound of claim 5.

22. A method of treating hypertension in a mammal consisting essentially of administering to a hypertensive mammal an antihypertensive amount of a compound of claim 6.

23. A method of treating hypertension in a mammal consisting essentially of administering to a hypertensive mammal an antihypertensive amount of a compound of claim 7.

24. A method of treating hypertension in a mammal consisting essentially of administering to a hypertensive mammal an antihypertensive amount of the compound of claim 8.

* * * * *